Figure 1:
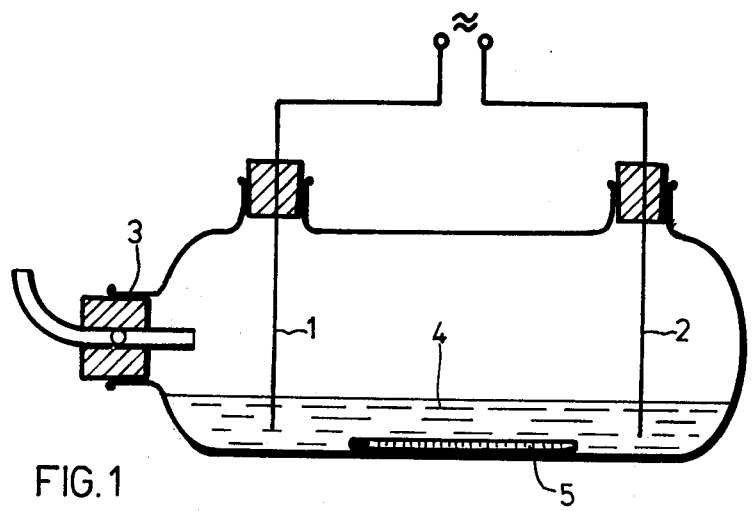

United States Patent [19]

Straub

[11] 4,188,375

[45] Feb. 12, 1980

[54] PROCESS FOR THE PREPARATION OF VACCINES

[75] Inventor: Otto C. Straub, Tuebingen, Fed. Rep. of Germany

[73] Assignee: Bayer Aktiengesellschaft, Leverkusen, Fed. Rep. of Germany

[21] Appl. No.: 835,923

[22] Filed: Sep. 23, 1977

[30] Foreign Application Priority Data

Sep. 25, 1976 [DE] Fed. Rep. of Germany ....... 2643213

[51] Int. Cl.² .................... A61K 39/02; A61K 39/12; C25F 5/00
[52] U.S. Cl. ........................................ 424/88; 422/22; 422/23; 204/131; 424/89; 424/90; 424/92; 435/173; 435/236
[58] Field of Search ..................... 195/1.2; 424/89, 88, 424/90, 92; 422/22, 23; 204/131

[56] References Cited

U.S. PATENT DOCUMENTS

| | | | |
|---|---|---|---|
| 2,428,329 | 9/1947 | Ham et al. | 422/22 |
| 2,955,076 | 10/1960 | Gossling | 422/22 |
| 3,058,894 | 10/1962 | Hallum | 204/131 |
| 3,594,115 | 7/1971 | Wesley et al. | 422/22 |
| 3,660,234 | 5/1972 | Gray | 195/1.2 |
| 3,753,886 | 8/1973 | Myers | 204/186 |

OTHER PUBLICATIONS

General Electric–Chem. Abst. vol. 66 (1967), p. 27408p.
Gilliland et al.–Chem. Abst. vol. 67 (1967), p. 97920u.
Hallum et al.–Chem. Abst. vol. 64 (1966), p. 10106e.
Hallum et al.–Chem. Abst. vol. 60 (1964), p. 2074c.

*Primary Examiner*—Sam Rosen
*Attorney, Agent, or Firm*—Sprung, Felfe, Horn, Lynch & Kramer

[57] ABSTRACT

A process has been developed for the preparation of (1) live and (2) inactivated vaccines which comprises subjecting a suspension of a micro-organism to an alternating electric current and, if desired, incorporating the micro-organisms into a vaccine preparation. The invention also includes the (1) live and (2) inactivated vaccines prepared by the processes of the invention.

10 Claims, 2 Drawing Figures

PROCESS FOR THE PREPARATION OF VACCINES

The present invention relates to processes for the preparation of vaccines (both of live and of inactivated vaccines).

It has already been disclosed that micro-organisms, especially bacteria and viruses, can be attenuated by a number of passages (tissue cultures or living animals or organs), whereupon these viruses and bacteria thus attenuated are still capable of multiplying, but have lost their pathogenic activity. Such attenuated viruses have still kept their immunogenic activity (live vaccines). The disadvantage of this attenuation process frequently described in the literature (see, for example, German Offenlegungsschrift (German Published Specification) No. 2,003,946) is, above all, the enormous expenditure of time and labour which is necessary before the desired degree of attenuation has been achieved by passaging. Thus, in the case of an attenuation via, for example 100 tissue culture passages, an attenuation time of about one year can be reckoned with.

Furthermore, it has been disclosed that micro-organisms, preferably bacteria and viruses, can be inactivated with the aid of chemical agents (so-called "inactivation agents"). A number of different chemical substances and classes of substances are possible inactivation agents, for example formaldehyde, ethyleneimine and its derivatives, glutaraldehyde, β-propiolactone, phenol, hydrogen peroxide and various others.

However, the known processes cannot always be applied to all micro-organisms in each case; the inactivation time with various inactivation agents (for example formaldehyde) is long in some cases.

Furthermore, it has been disclosed that inactivation of micro-organisms can be carried out, for example, by the action of heat or ultraviolet light.

Inactivation processes known hitherto have disadvantages, which in some cases are different; thus, in some cases the structure determining the antigenic activity of micro-organisms, for example viruses, is too extensively destroyed. Furthermore, it is sometimes difficult to bring about complete destruction of the infectious properties of the micro-organisms and at the same time to retain the antigenic properties. In some cases it is possible, through recombination and/or mutation, that certain inactivated microorganisms regain their infectious properties under certain circumstances. In addition, for example when carrying out the inactivation with formaldehyde or with the action of ultraviolet light, there is the danger of aggregate formation, portions of the infectious micro-organisms not being activated under certain circumstances.

According to the present invention micro-organisms, particularly bacteria and viruses but also mycoplasms and chlamydia, are attenuated or inactivated by treatment in suspension in a field of an alternating electric current.

The invention therefore provides a process for the preparation of a vaccine which comprises subjecting a suspension of a micro-organism to an alternating electrical current and incorporating the micro-organism into a vaccine preparation.

The invention also includes attenuated or inactivated micro-organisms prepared by the method of the invention and vaccine preparations incorporating the said microorganisms. The vaccine preparations usually contain an auxiliary material, such as a solid or liquefied gaseous diluent or carrier or a liquid diluent or carrier containing a surface active agent. In particular, the vaccine preparation may be in the form of a sterile and, where appropriate, blood isotonic aqueous solution or suspension. The disadvantages described above of the attenuation or inactivation processes which have been disclosed hitherto are avoided by preparing live or inactivated vaccines by the process according to the invention. The process according to the invention is carried out in a reaction vessel under sterile conditions. The apparatuses described in FIGS. 1 and 2 can be used for this purpose.

The apparatus shown in FIG. 1 consists of a flat glass bottle with three orifices. The orifice at the neck of the bottle (③) is closed by a stopper containing an outlet tube with a valve and the other two orifices are also closed by stoppers through which electrodes of a noble metal (for example gold, platinum or silver, preferably silver, but noble metal alloys are also possible), which are connected to a source of an alternating electric voltage, are passed. ①, ②. A thermometer is located in the bottle for monitoring. ⑤

The suspension of the micro-organism to be treated with the alternating electric current is in the glass vessel. The experimental conditions to be chosen (temperature, period of treatment with the alternating electric current, alternating voltage, current strength, pH value and the like) depend on the nature of the micro-organism to be treated and the intended effect of the process according to the invention (for example attenuation to give live vaccine or inactivation to give inactivated vaccine). In addition, in some cases there is coupling of the action of the individual factors so that a lower current strength, for example, can be compensated for by a longer period of action of the alternating current.

In order to achieve higher voltage and current strength values, the vessel can also be provided with a cooling jacket.

Figure 2:
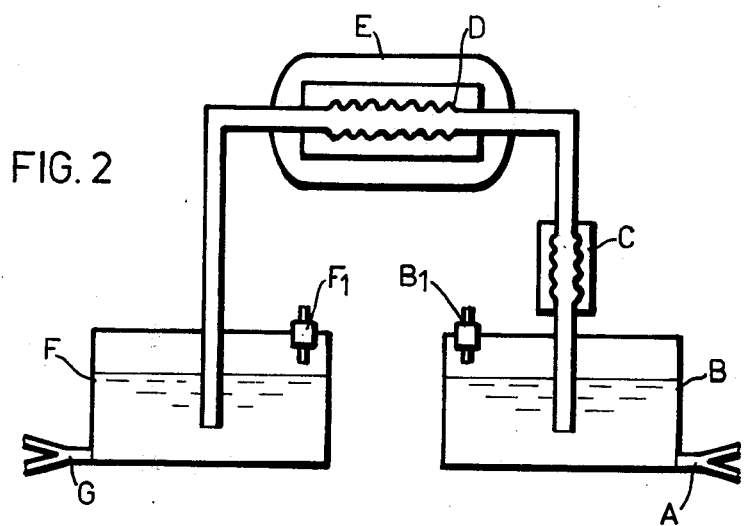

The apparatus for the so-called flow process is represented in FIG. 2.

In this process, the suspension of micro-organisms to be treated flows into the vessel (B) via a two-way cock (A) provided with a valve. The suspension of micro-organisms is pumped over the electrodes (D), which are provided with a cooling jacket (E) if appropriate, via the two-way pump (C). The outlet from the vessel (F) is preferably effected via a two-way cock (G) provided with a valve. $B_1$ and $F_1$ denote devices for the air supply and withdrawal respectively. In this procedure, sterile air is appropriately employed.

The flow system outlined in FIG. 2 is very well suited to the preparation of vaccines (both live and inactivated vaccines).

All the substances which can also be otherwise converted into live or inactivated vaccines by attenuation via tissue culture or animal passages or by inactivation with the aid of chemical and physical methods can be used as micro-organisms in the process according to the invention.

Examples which may be mentioned are: RNA-viruses of the following groups: rod-shaped plant viruses, picorna viruses, toga viruses, rhabdo-viruses, retroviridae, arena viruses, orthoamyxo-viruses, paramyxo-viruses, corona and orbi viruses and two Ostrand RNA-viruses, and DNA-viruses of the following groups: small DNA-phages, parvo-viruses, reoviruses, adeno-viruses, papova-viruses, phages of medium size, large phages, herpes viruses, iridoviridae viruses, paravaccinal viruses, vaccina viruses and adeno-concomitant viruses.

Bacteria which can be used which may be mentioned are: bacteria of the order Eubacteriales (unramified bacteria), preferably of the genera Neisseria, Streptococcus, Leuconostoc, Pseudomonas, Escherichia, Serratia, Proteus, Salmonella, Pasteurella, Brucella, Haemophilus, Corynebacterium and Clostridium; and bacteria of the order Actinomycetales, preferably of the genus Streptomyces, and bacteria of the order Spirochaetales, preferably of the genus Leptospira.

If it is desired to prepare attenuated, that is to say non-pathogenic but still completely immunogenic, live microorganisms in the form of live vaccines, the following process conditions, as a function of the micro-organism employed, have proved appropriate:

Alternating voltage: in general, the process is appropriately carried out with the existing mains voltage, which was 220 V in the experiments carried out in the scope of the present Application, but it is also possible, of course, to carry out the process with other voltage values, for example 110 or 330 V. In such a case, the other reaction conditions are to be adjusted.

Current strength: a current strength of 200 to 300 mA with an alternating voltage of 220 V has proved appropriate. Of course, other current strength values are also possible as a function of the voltage and of the nature of the solution.

Temperatures: in general, the treatment with the alternating electric current is carried out at temperatures from about 4° to 60° C., preferably at about 20° to 40° C. and in particular at about 37° C. to 39° C. (physiological temperature range). The temperature used depends, for example, on the heat stability of the micro-organism employed.

The temperature of the micro-organisms or suspensions of micro-organisms to be treated can be adjusted, whilst the voltage remains constant, by varying the current strength in such a manner that there is a constant temperature value in the suspension of micro-organisms to be treated.

Period of Treatment with the Alternating Electric Current

A treatment time of about 5 to 300 minutes, in particular of about 30 to 240 minutes, has proved appropriate in the case of treatment for the purpose of preparing live vaccines based on attenuated micro-organisms (preferably bacteria and viruses). However, time values less than 5 or more than 300 minutes are possible, depending on the nature of the micro-organism employed and the other experimental conditions used (such as, for example, temperature, suspending agent, voltage and current strength).

In addition, the degree of attenuation which is to be achieved, measurable by animal experimental methods which are in themselves known, is of importance.

If it is desired to prepare, with the aid of the process according to the invention, inactivated micro-organisms for use in inactivated vaccines, the same statements in respect to alternating voltage, current strength and temperatures in the preparation of attenuated micro-organisms for use in live vaccines apply.

Thus, in the case of the inactivation of micro-organisms, the process for the treatment of micro-organisms with an alternating electric current is the same as that in the case of the attenuation of micro-organisms.

However, in general the inactivation by the process according to the invention requires more time and energy.

Thus, in general, the inactivation procedure by the process according to the invention (see FIG. 1) lasts about 10 to 72 and preferably about 15 to 48 hours. However, values below 10 and above 72 hours are possible, depending on the nature of the micro-organism employed and the other experimental conditions used (such as, for example, the flow process (FIG. 2), temperature, suspending agent, voltage and current strength.

In general, aqueous suspensions of the abovementioned micro-organisms are employed as starting materials for the process according to the invention. Those media in which the micro-organisms to be treated are cultured, such as, for example, Earle's medium, optionally with the addition of lactalbumin hydrolysate, or the following other media: Eagle's medium, Hanks medium, medium PM-13 (Serva), VM-3a medium, MEM medium and the like, are preferably used.

The end products, which contain attenuated or inactivated micro-organisms, obtained after the treatment with the alternating electric current are either administered as such in the sterile form of are formulated to give live or inactivated vaccines, by methods which are in themselves known and are customary, and are administered as a solution, syrup, emulsion, suspension, spray, ointment, paste, cream, lotion, aerosol, tablets and the like.

The formulations are prepared in a manner which is in itself known, for example by diluting the micro-organisms, attenuated or inactivated according to the invention, with suitable solvents and/or inert non-toxic, solid semi-solid or liquid excipients, if appropriate, using emulsifying agents and/or dispersing agents, spraying agents and propellents and using suitable stabilisers.

Solvents, excipients, emulsifying agents and dispersing agents which may be mentioned here are: water, non-toxic organic solvents or diluents, such as paraffins (for example petroleum fractions), vegetable oils (for example groundnut oil/sesame oil), polyhydric alchohols, such as, for example, trihydric alcohols, i.e. glycerol and glycols (for example propylene glycol and polyethylene glycol) and water; solid excipients, such as, for example, natural rock powders (for example highly disperse silica and silicates) and sugars (for example cane sugar, lactose and glucose); emulsifying agents, such as non-ionic and anionic emulsifiers (for example polyoxyethylene-fatty acid esters, polyoxyethylene-fatty alcohol ethers, alkylsulphonates and arylsulphonates), dispersing agents (for example lignin, methylcellulose, starch and polyvinylpyrrolidone) and lubricants (for example magnesium stearate, talc, stearic acid and sodium lauryl-sulphate).

Stabilisers which may be mentioned are: amino-acids, sugars, proteins, polysaccharides and polyalkylene glycols. These stabilisers can be added both in aqueous solution and in the lyophilised state.

The viruses and bacteria attenuated according to the invention or the medicaments obtained from these according to the invention can be used in the customary manner, for example intranasally, intragenitally, orally, intramuscularly, intravenously and subcutaneously (locally, in particular on all mucous membranes of the human body and animal body).

The amount of administered in the treatment of the human organism and animal organism must be determined from case to case. However, as a rule it corresponds to the vaccine amounts prepared by the classical process (for example $10^5CID_{50}$ per ml or g).

The abbreviations used in the examples which follow have the following meaning: IBR/IPV-viruses: infectious bovine rhinotracheitis/infectious pustulous vulvovagenitis PI-3 virus: parainfluenza-3 virus MD-VD-virus: mucosal disease-virus, diarrhoea virus HAH: haemagglutination-inhibiting

EXAMPLE 1

A virulent IBR-IPV virus isolated from the respiratory tract of a diseased animal was cultivated on a calf liver cell culture in Earle's medium, with the addition of lactalbumin hydrolysate, at 37° C. for 48 hours. The IBR-IPV-virus suspension thus obtained was freed from the cell residues by centrifuging at 4° C. and 2,000 g and was then exposed to a field of an alternating electric current (220 V alternating voltage, current strength 260 m A, silver electrodes) at 22° C. for 1 hour in the reaction vessel outlined in FIG. 1.

For the control, the same amount of IBR-IPV-virus is stored in the culture medium (Earle's medium) at 22° C.

Thereafter, four cattle each, in an isolation stall, were infected with the two suspensions.

Result: Whilst the control animals exhibited all the symptoms of rhinotracheitis, no disease symptoms at all could be detected in the cattle infected with the suspension treated as above. In the tissue culture, it could be shown that (1) both the virus suspension treated with the alternating electric current and the untreated virus suspension used as a control exhibited a cytopathogenic effect and that (2) four weeks later both groups of animals had specific neutralising antibodies in the serum.

Thus, in the case of the virus suspension treated with the alternating electric current, a live vaccine is present which contains apathogenic IBR-IPV virus.

EXAMPLE 2

A parainfluenza-3 virus strain was isolated from the respiratory tract of diseased cattle and multiplied on secondary calf liver cells in Earle's medium, with the addition of 0.5% of lactalbumin hydrolysate and 3% of inactivated calf serum free from antibodies. After centrifuging off the cell debris, the active PI-3-virus suspension was exposed to a field of an alternating electric current (220 V alternating voltage, current strength 255 mA, silver electrodes) for 1 hour at 37° C.

With the aid of the tissue culture technique, it can then be established that a virus which is capable of multiplying is present in the suspension (presence of a so-called "live vaccine").

The animal experimental test with the PI-3-virus strain treated according to the invention showed the same results as described in Example 1, that is to say the cytopathogenic effect could be detected and in addition specific neutralising and HAH-R-antibodies could be detected in the blood serum of the treated animals.

EXAMPLE 3

Analogously to the procedure described in Example 1, an aqueous suspension of a virulent IBR-IPV-virus is exposed to a field of an alternating electric current (220 V alternating voltage, 250 mA current strength, silver electrodes) at 37° C. for 24 hours. An IBR-IPV inactivated vaccine was then present.

The virus suspension thus obtained was placed onto a calf liver culture and incubated for up to 5 days at 37° C. With this procedure, a cythopathogenic effect could no longer be observed.

EXAMPLE 4

85 ml of the virus suspension obtained according to Example 3 are mixed with 15 ml of a 3% strength $Al(OH)_3$ suspension. In each case 10 ml of the resulting vaccine are administered subcutaneously to 3 cattle free from IBR-IPV-antibodies.

After 20 days, IBR-IPV-antibodies could be detected in the blood serum of all 3 cattle.

On the 21st day, the 3 vaccinated cattle and a nonvaccinated control animal were each infected intranasally with 2 ml of the active IBR-IPV-virus suspension, described in Example 1, which has not been exposed to the alternating electric current.

Whilst the control animal showed all the symptoms of acute rhinotracheitis, no disease symptoms at all could be detected in the 3 vaccinated cattle.

EXAMPLE 5

Analogously to Example 1, a suspension of virulent MD-VD-virus in Eagle's medium was exposed to a field of an alternating electric current (220 V alternating voltage, current strength 260 mA, silver electrodes) at 37° C. for 32 hours.

The MD-VD-virus suspension thus obtained proved to be completely inactivated, that is to say no ythopathogenic effect could be detected.

However, the immunogenic properties were retained (specific antibody formation, identity in the double diffusion test).

What is claimed is:

1. A process for the preparation of a vaccine which comprises subjecting, at a temperature of from 4° to 60° C. a suspension of the micro-organism to an alternating electrical current having a voltage of from 110 to 330 V and a strength of from 200 to 300 mA, and incorporating the resulting inactivated or attenuated micro-organism into a vaccine preparation.

2. A process of claim 1 wherein the suspension is further treated to isolate the treated micro-organism.

3. A process of claim 1 wherein the microorganism is subjected to the alternating current in the presence of a culture medium.

4. A process of claim 1 wherein the treatment is effected for from about 5 to 300 minutes to obtain a live vaccine or for from 10 to 72 hours to obtain an inactivated vaccine.

5. A process of claim 1 wherein the treatment of the micro-organism is carried out in apparatus substantially as described in FIG. 1 of the drawings.

6. A vaccine preparation incorporating an attenuated micro-organism processed according to claim 1 and a carrier or diluent therefor.

7. A vaccine preparation incorporating an inactivated micro-organism processed according to claim 1 and a carrier or diluent therefor.

8. A vaccine preparation of claim 6 further comprising a solid or liquefied gaseous diluent or carrier, or a liquid diluent or carrier containing a surface active agent.

9. A vaccine preparation of claim 6 in the form of a sterile aqueous solution or suspension.

10. A process according to claim 1 wherein the treatment of the micro-organism is carried out in apparatus substantially as described in FIG. 2 of the drawings.

* * * * *